(12) United States Patent
Thompson

(10) Patent No.: US 6,770,122 B2
(45) Date of Patent: Aug. 3, 2004

(54) COPPER DEPOSITION USING COPPER FORMATE COMPLEXES

(75) Inventor: Jeffery Scott Thompson, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 43 days.

(21) Appl. No.: 10/317,979

(22) Filed: Dec. 12, 2002

(65) Prior Publication Data

US 2003/0165623 A1 Sep. 4, 2003

Related U.S. Application Data

(60) Provisional application No. 60/340,631, filed on Dec. 12, 2001.

(51) Int. Cl.$^7$ .......................... C23C 16/18; B05D 3/02; B01J 31/18; C07F 1/08
(52) U.S. Cl. ............. 106/1.18; 106/287.2; 106/287.21; 427/376.1; 502/167; 556/116
(58) Field of Search .............................. 106/1.18, 287.2, 106/287.21; 427/376.1; 502/167; 556/116

(56) References Cited

U.S. PATENT DOCUMENTS

| | | | | |
|---|---|---|---|---|
| 3,771,973 A | * | 11/1973 | Miller | 428/625 |
| 3,980,654 A | * | 9/1976 | Gysling | 546/2 |
| 4,582,731 A | | 4/1986 | Smith | |
| 4,622,069 A | * | 11/1986 | Akai et al. | 106/1.11 |
| 4,761,467 A | * | 8/1988 | Bhattacharya | 558/277 |
| 4,818,255 A | * | 4/1989 | Matsuura et al. | 95/44 |
| 5,767,303 A | * | 6/1998 | Minami et al. | 558/275 |
| 5,789,027 A | | 8/1998 | Watkins et al. | |
| 2003/0148024 A1 | * | 8/2003 | Kodas et al. | 427/125 |

OTHER PUBLICATIONS

Escriva, J. Chem. Soc. Dalton Trans., "Synthesis, crystal structure and magnectic properties of [[Cu(tzq)2)] 2(u–HCO2)2]–4HWO (tzq–[1,2,3]triazolo[1m,5–a]quinoline), a binuclear copper(II) complex with unusual monoatomic formate bridges", 1997, pp. 2033–2038, Spain, no month available.

Darr, et al., American Chemical Society, "Directions in Inorganic and Metal–Organic Coordination Chemistry in Supercritical Fluids", 1999, pp. 495–541, vol. 99, No. 2, England, no month available.

Borel et al., Revue de Chimie minerale, "Un complexe carboxylato–cuivre II de structure carree: le trans diformato, bis(dimethyl 2–6 pyridine) cuivre II", (1980) pp. 202–208, France, no month available.

Cross, et al. Ind. Eng. Chem. Res. Determination of Metal–Chelate Complex Solubilities in Supercritical Carbon Dioxide, (1996) pp. 1765–1770, vol. 35, Texas, no month available.

Smart, et al., Talanta, Solubility of chelating agents and metal–containing compounds in supercritical fluid carbon dioxide, (1997) pp. 137–150, vol. 44, UK, no month available.

Hsu, et al., Chemical Vapor Deposition, "Self–Reducible Cu Source Reagents for the CVD of Copper", (2001) pp. 28–31, vol. 1, no month available.

Bernard, et al., Thermochimica Acta, Elude de quelques Composes Du Formiate De Cuivre Solvate Par Limidazole Et Le Methyl–1–Imidazole, (1996) pp. 139–145, vol. 98, Amsterdam, no month available.

* cited by examiner

Primary Examiner—Helene Klemanski

(57) ABSTRACT

The present invention relates to novel copper formate complexes and the deposition of metallic copper on substrates or in or on porous solids using these novel copper complexes.

12 Claims, 2 Drawing Sheets

Figure 1. Molecular Structure of [Cu(1-methylimidazole)$_2$(HCOO)$_2$]$_2$
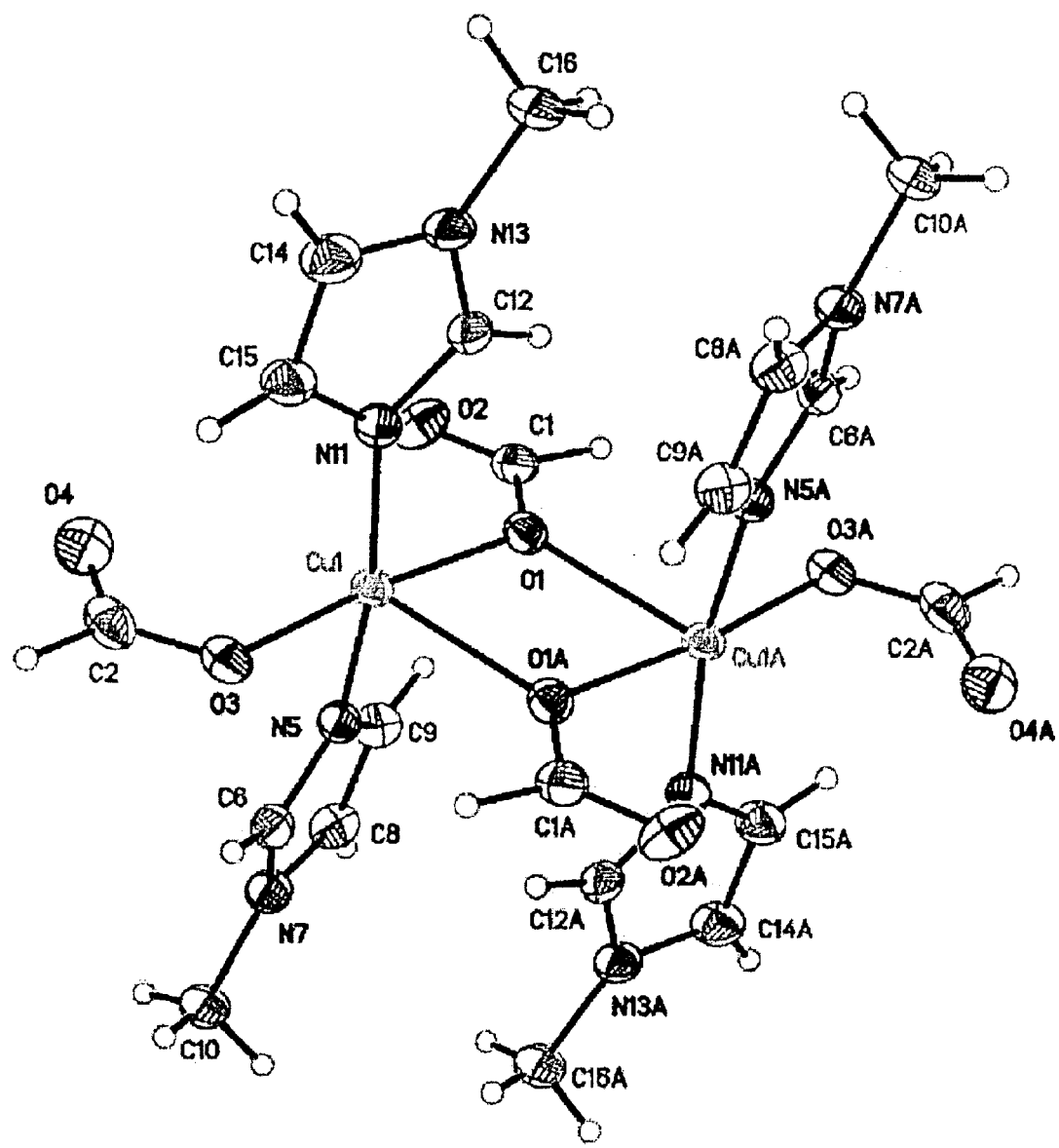

Figure 2. Structure of Cu(1-butylimidazole)$_2$(HCOO)$_2$.
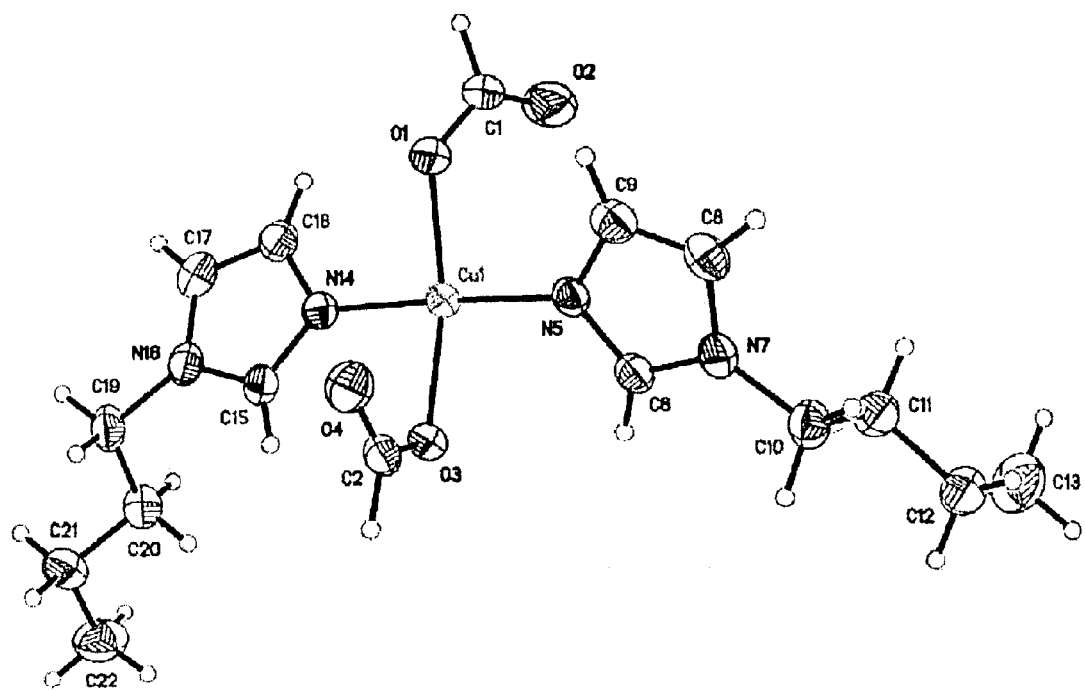

COPPER DEPOSITION USING COPPER FORMATE COMPLEXES

FIELD OF THE INVENTION

The present invention relates to novel copper formate complexes and the deposition of metallic copper on substrates or in or on porous solids using such copper formate complexes.

TECHNICAL BACKGROUND

The deposition of copper from supercritical fluids has been described. Watkins and McCarthy, U.S. Pat. No. 5,789,027, used an external reducing agent such as hydrogen added to the supercritical fluid to promote copper deposition on a substrate (e.g., silicon wafer). Also, copper disproportionation reactions have been used (Hsu et al., *Chemical Vapor Deposition*, 2001, 7, No. 1, pp. 28–31).

Bernard et al. (*Thermochimica Acta*, 98, 139–145 (1986)) describe the formation of dimeric copper (ll) complexes with 1-methylimidazole by addition of copper formate to an ethanol solution containing an excess of 1-methylimidazole. The product precipitates rapidly from solution. It contains Cu(II) ions coordinated to three or four imidazole groups and water molecules. The formate ion is present as counter ion and does not coordinate to the copper ion. This formulation is unsuitable for use in supercritical fluids such as supercritical carbon dioxide because the copper complex has little or no solubility in non-polar solvents.

Escrivá et al. (*J. Chem. Soc. Dalton Trans.*, 2033–2038 (1997)) describe a formate complex with monoatomic bridging formates.

Borel et al. (*Rev. Chim. Miner.*, 17, 202–208 (1980)) describe the preparation and structure of a mononuclear copper formate complex with 2,6-lutidine.

Smith (U.S. Pat. No. 4,582,731) describes solid films deposited by dissolving a solid material into a supercritical fluid solution at an elevated pressure and then rapidly expanding the solution through a short orifice into a region of relatively low pressure.

Darr and Poliakoff (*Chemical Reviews*, 99, 495–542 (1999)) have shown that compounds soluble in hexane exhibit solubility in supercritical carbon dioxide and have described metal ligands that have been used for metal solubilization and extraction in supercritical fluids.

Smart et al. (*Talanta*, 44, 137–150 (1997)) have described the preparation of Cu(II) complexes which are soluble in supercritical carbon dioxide.

Cross et al. (*Ind. Eng. Chem. Res.*, 35, 1765–1770 (1996)) describe the use of co-solvents in supercritical carbon dioxide to dissolve metal complexes.

Trofimenko ("Scorpionates", Imperial College Press, 1999) reviews substituted pyrazole derivatives.

SUMMARY OF THE INVENTION

This invention provides a composition comprising copper, two formate ions coordinated to the copper, and two aromatic nitrogen heterocyclic ligands coordinated to copper through nitrogen, wherein the aromatic nitrogen heterocyclic ligands are selected from the group consisting of $C_{10}$–$C_{20}$ alkyl-substituted pyridines, $C_9$–$C_{20}$ alkyl-substituted pyrazoles, $C_9$–$C_{20}$ alkyl-substituted imidazoles and $C_9$–$C_{20}$ alkyl-substituted triazoles, in which the N1 position of the pyrazole, imidazole and triazole ligands are alkyl-substituted.

A process for deposition of metallic copper on a substrate or in or on a porous solid is also provided, comprising
a. contacting the substrate or porous solid with a copper complex of this invention to form a copper complex-coated substrate; and
b. heating the copper complex-coated substrate or porous solid to about 70° C. to about 200° C. to form a deposit of metallic copper on the substrate.

BRIEF DESCRIPTION OF THE DRAWINGS

FIG. 1 is the molecular structure of [Cu(1-methylimidazole)$_2$(HCOO)$_2$]$_2$ and FIG. 2 is the molecular structure of Cu(1-butylimidazole)$_2$(HCOO)$_2$.

DETAILED DESCRIPTION

This invention provides novel copper-formate complexes which are useful as precursors for the deposition of metallic copper. This invention is particularly useful for deposition of electronic interconnect layers in microcircuitry as well as decorative arts, corrosion and wear control, catalysis, optics and others areas of technology.

The copper formate complexes of this invention can be prepared from a wide range of aromatic nitrogen heterocyclic ligands. The preferred synthesis at room temperature of the copper formate complexes begins with mixing copper formate in methanol at a concentration between 0.01 and 1 moles of copper formate per liter. This frequently forms a slurry rather than a solution. Preferably, anhydrous copper formate is used. The selected ligand is added directly, if the ligand is a liquid, or as a solution in methanol or diethyl ether at concentration of 0.01 to 1 molar. The ligand or ligand solution is added rapidly, typically in less than 10 minutes on a laboratory scale. The solution is stirred until the formate dissolves and then is filtered through diatomaceous earth to remove excess formate. The solvent is then removed under vacuum.

Suitable ligands for use in this invention are aromatic nitrogen heterocyclic ligands selected from the group consisting of $C_{10}$–$C_{20}$ alkyl-substituted pyridines, $C_9$–$C_{20}$ alkyl-substituted pyrazoles, $C_9$–$C_{20}$ alkyl-substituted imidazoles and $C_9$–$C_{20}$ alkyl-substituted triazoles, in which the N1 position of the pyrazole, imidazole and triazole ligands are alkyl-substituted.

Preferred ligands include pyridines of Formula I:

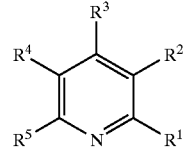

Formula I wherein
$R^1$ and $R^5$ are selected from the group consisting of H and $C_1$–$C_4$ alkyl;
$R^2$ and $R^4$ are selected from the group consisting of H, $C_1$–$C_4$ straight-chain alkyl, and $C_6$–$C_{15}$ branched alkyl comprising at least one branch of at least four carbons; and
$R^3$ is selected from the group consisting of H, $C_1$–$C_{15}$ straight chain alkyl and $C_6$–$C_{15}$ branched alkyl with at least one branch with at least four carbons in each branch;
with the provisos that at least one of $R^2$, $R^3$ and $R^4$ is $C_4$–$C_{15}$;

if $R^1$, $R^2$, $R^4$, and $R^5$ are each H, then $R^3$ is a $C_6-C_{15}$ straight chain alkyl or a nonyl branched alkyl, where at least one of the branches contains at least four carbons;

if either $R^1$ or $R^5$ is $C_4$ alkyl, then the other is H; and if $R^3$ is H or $C_1$, then at least one of $R^2$ and $R^4$ is $C_4-C_{15}$ straight chain alkyl or $C_6-C_{15}$ branched alkyl.

Preferred ligands also include pyrazoles of formula II:

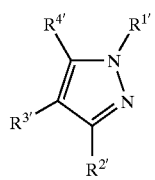

Formula II wherein, $R^{1'}$ is selected from the group consisting of Me and $C_6-C_{17}$ straight-chain alkyl and $C_6-C_{17}$ branched alkyl, with branches of at least four carbon atoms;

$R^{2'}$ and $R^{4'}$ are selected from the group consisting of H, $C_1-C_4$ straight-chain alkyl, and $C_3-C_4$ branched alkyl; and $R^{3'}$ is selected from the group consisting of H, $C_1-C_4$ straight-chain alkyl, $C_3-C_4$ branched alkyl, $C_6-C_{17}$ straight-chain alkyl and $C_6-C_{17}$ branched alkyl, with branches of at least four carbon atoms;

with the proviso that if $R^{2'}$, $R^{3'}$ and $R^{4'}$ are H, then $R^{1'}$ is $C_{10}-C_{17}$ straight chain alkyl or $C_6-C_{17}$ branched alkyl with branches of at least 4 carbon atoms.

Preferred ligands also include imidazoles of formula III:

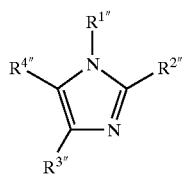

Formula III wherein, $R^{1''}$ is selected from the group of $C_1-C_8$ straight-chain alkyl and $C_6-C_8$ branched alkyl with at least one branch of at least four carbons;

$R^{4''}$ is selected from the group consisting of H, $C_1-C_8$ straight chain alkyl, and $C_6-C_8$ branched alkyl with at least one branch of four carbons; and $R^{2''}$ and $R^{3''}$ are selected from the group consisting of H, $C_1-C_4$ straight chain alkyl, and $C_3-C_4$ branched alkyl, with the provisos that at least one of $R^{1''}$ and $R^{4''}$ is $C_6-C_8$; and if $R^{2''}$, $R^{3''}$ and $R^{4''}$ are H, then $R^{1''}$ is $C_6-C_8$ branched alkyl with at least one branch of at least four carbons.

Preferred ligands also includes triazoles of Formula IV:

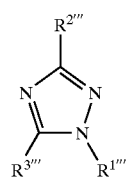

Formula IV wherein, $R^{1'''}$ is selected from the group consisting of $C_8-C_{18}$ straight chain alkyl and $C_7-C_{18}$ branched alkyl with at least one branch of at least four carbons; and $R^{2'''}$ and $R^{3'''}$ are selected from the group of H and $C_1-C_2$ alkyl.

The selected ligands produce complexes that are stable at room temperature and decompose at reasonable temperatures as determined by thermal gravimetric analysis. The formation of monomeric or dimeric complexes depends on the steric bulk of the ligand. Copper (II) formate complexes of this invention are derived from monodentate nitrogen donating ligands selected from the group consisting of pyridines, pyrazoles, imidazoles, and triazoles. The nitrogen donating ligand must be able to coordinate to the copper ion through the lone pair on the nitrogen atom. The nitrogen atom must be available for coordination. Thus, bulky tertiary non-aromatic nitrogen donor ligands (e.g., triethylamine) are not suited as because of the steric bulk at the tertiary nitrogen atom. Primary and secondary amines do form complexes, but are not suitable as ligands because N–H groups result in the formation of unwanted byproducts. Aromatic, heterocyclic amines are most suitable. Imidazoles, pyridines, pyrazoles, and triazoles form complexes, provided the steric bulk around the coordinating nitrogen atom is not hindering. 4-t-butylpyridine forms a formate complex, but 2,6-diphenylpyridine does not.

Although some copper formate complexes of this invention are oils and can be used in pure form for the deposition of copper, it is preferred to dissolve the copper formate complexes in a non-polar solvent. Supercritical carbon dioxide is a preferred solvent, and may be mixed with a suitable co-solvent.

For use in supercritical carbon dioxide, the ligands must be selected such that the ligand and its complex have reasonable solubility in supercritical carbon dioxide. In this invention, solubility is achieved by use of ligands that contain alkyl groups of six or more carbons. This avoids the use of fluorine-containing ligands and the inevitable contamination of sensitive electronic components with fluoride ion originating from such ligands. The use of long-chain and/or branched alkyl groups provides Cu(II) complexes with sufficient solubility, above 10 $\mu$M in hexane, to be useful in a deposition process. Multiple alkyl groups on the heterocyclic ring can also be used to achieve solubility.

Structure 1 shows a copper formate complex with 1-octyl-3,5-dimethylpyrazole. For comparison, Structure 2 shows a copper formate complex with 1-octylpyrazole. The copper formate complex prepared from 1-octyl-3,5-dimethyl pyrazole is soluble, whereas the 1-octylpyrazole-Cu(II) complex shows no solubility in hexane and therefore no solubility in supercritical carbon dioxide. (Hexane solutions with the 1-octylpyrazole-Cu(II) complex show no blue color, which indicates that the solubility is 10 $\mu$M or less.) Both of the methyl groups (or other alkyl groups) and an alkyl chain of suitable length are required to achieve sufficient solubility in hexane and supercritical carbon dioxide. The copper complex with 1-hexyl-3,5-dimethylpyrazole is less soluble in hexane than the copper complex of 1-octyl-3,5-dimethylpyrazole, based on the intensity of the blue solution color. Longer alkyl chains and branched chains of suitable length in the 1-position of the pyrazole ring will yield soluble complexes. The copper complex with 1-(2-hexyl)-3,5-dimethylpyrazole is soluble in hexane, as shown by the blue color of the solution. Derivatives with 3,4,5-trimethyl or other 3,5-substituted pyrazoles described in the literature (Trofimenko), which allow coordination of both pyrazole rings to the copper formate moiety, will also be suitable for this application.

Structure 1

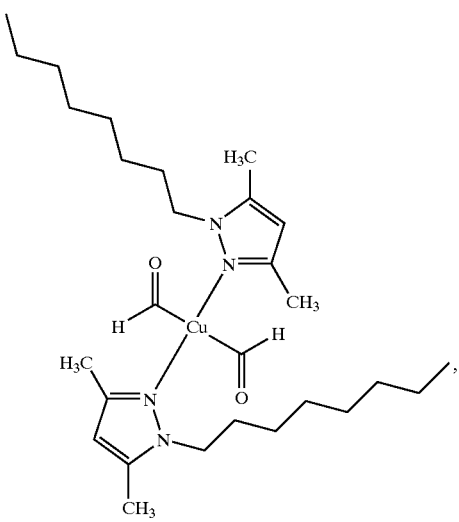

1-octyl-3,5-dimethylpyrazole copper formate complex

Structure 2

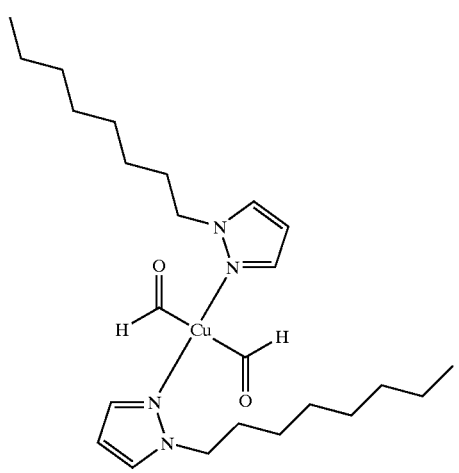

1-octylpyrazole copper formate complex

Copper formate complexes were prepared using 1-octyl-2-ethyl-4-methylimidazole and 1-hexyl-2-ethyl-4-methylimidazole as ligands. The Cu(II) complex with the 1-octyl group dissolves in hexane to yield a blue solution, whereas there is no color development with complexes with the 1-hexyl group. Applicants theorize that the hexyl group is not long enough to shield the ionic copper inner-coordination sphere from the solvent. The combination of the alkyl groups in the 2 and 4 positions and the octyl group in the 1-position allow the copper inner coordination sphere to be surrounded by coordination of two of these imidazole groups. Longer chains will yield soluble compounds as well.

A common technique used in dissolving metal complexes in supercritical carbon dioxide is to add a co-solvent (Cross et al.). The requirements of a co-solvent have been defined (Cross et al.). Methanol and other alcohols are commonly used. Compounds showing little or no solubility in hexane or supercritical carbon dioxide can be dissolved with addition of methanol. Hexane solutions of the Cu(II) formate complex with 1-hexyl-2-ethyl-4-methylimidazole do not develop the characteristic blue color of Cu(II)-formate complexes in solution, but mixing of a methanolic solution of this complex into hexane yields a blue solution. Similar results are obtained with 4-t-butylpyridine and with 1-butanol in place of methanol. Table 1 lists ligands that give rise to soluble compounds with addition of a co-solvent. In these measurements, the complex was dissolved in 0.25–1 mL of methanol or 1-butanol and then shaken with 5–10 mL hexane; solubility was indicated by formation of a homogeneous blue solution. Alcohols such as methanol and 1-butanol are totally miscible with supercritical carbon dioxide at ambient temperatures and high pressure (Cross et al). Between 2 to 5% cosolvent is typically used in order to retain supercritical properties of the solvent at reasonable temperatures and pressures.

TABLE 1

Nitrogen donating ligands (complexes soluble in supercritical carbon dioxide with co-solvent or in hexane with co-solvent)

| Ligand Family | Compounds |
| --- | --- |
| Pyridine derivatives | 4-(5-nonylpyridine); 4-t-butylpyridine |
| Imidazole derivatives | 1-octyl-2-ethyl-4-methylimidazole; 1-(2-ethylhexyl)-2-ethyl-4-methylimidazole 1-hexyl-2-ethyl-4-methylimidazole |
| Pyrazole derivatives | 1-octyl-3,5-dimethylpyrazole 1-(2-ethylhexyl)pyrazole 1-hexyl-3,5-dimethylpyrazole 1-octylpyrazole |

The derivative with 4-(5-nonyl)pyridine is the preferred complex for use with supercritical carbon dioxide. The copper complex with this pyridine is a deep blue oil at room temperature. Spectroscopic and analytical data are consistent with the formulation $Cu(L)_2(HCOO)_2.H_2O$. Each copper is coordinated to two pyridine groups. The complex has a neutral charge. The complex shows good solubility in hexane (38 wt %) and supercritical carbon dioxide (4.3 wt %).

Deposition of metallic copper can be accomplished by contacting the substrate or porous solid with the copper formate complex by such means as brushing or dipping. The material is then heated to 70° C. to 150° C.

In a preferred embodiment, the precursor is deposited on the substrate or in or on a porous solid by contact with a solution of copper formate complex in a supercritical fluid. Smith (U.S. Pat. No. 4,582,731) describes a method and apparatus for depositing a solid material on a substrate from supercritical solution and is hereby incorporated by reference. To obtain the desired metallic copper coating, the deposited copper formate complex is heated on the substrate or in or on the porous solid to the decomposition temperature of between 70 and 200° C.

Although not wanting to be bound by theory, Applicants believe that the copper deposit on a substrate is formed from the precursor by reduction of the copper ion by a coordinated formate. In these reactions one equivalent of carbon dioxide is released per copper. The second formate is most likely released as formic acid or in combination with one of the basic aromatic nitrogen heterocyclic ligands. With such an internal reducing agent, there is no need to add a second compound to reduce the Cu(II) ion to copper metal. This offers a substantial advantage over other copper deposition methods disclosed in the prior art.

EXAMPLES

All manipulations were performed in a Vacuum Atmospheres dry box under dry nitrogen gas. Copper formate hydrate was obtained from Aldrich (Milwaukee, Wis., USA 53233-2681; Catalog No. 40,494-2). This material was dried by heating at 55–65° C. under vacuum for two days and was stored under nitrogen. 4-(5-nonyl)pyridine was obtained from TCI America (Portland, Oreg., USA 97203; Catalog No. N0496) and was deaerated with nitrogen prior to use. Diatomaceous earth was obtained from Johns Manville Engineered Products Group, P.O. Box 5108, Denver, Colo. 80217 USA. Solvents were reagent grade or better, deaerated with nitrogen, and stored over activated 4 Å molecular sieves. Elemental analyses were performed by Micro-Analysis Inc., Wilmington, Del., USA 19808.

EXAMPLE 1

Synthesis of Copper(II) Complex with 4-(5-nonyl) pyridine

Anhydrous copper formate (0.025 g, 0.163 mmole) was mixed with 5 mL methanol in a round bottom flask with a Teflon-coated stir bar. 4-(5-nonyl)pyridine (0.072 mL, 0.326 mmole) was added directly to the stirred solution. A deep blue color developed rapidly. The mixture was stirred for five minutes and filtered through diatomaceous earth to remove excess copper formate. The solvent was removed under vacuum to yield royal blue oil. Elemental analysis was consistent with the formation of $Cu(4-(5-nonyl)pyridine)_2$ $(HCOO)_2.H_2O$. Calculated: 61.88% C; 8.66% H and 4.81% N. Observed: 61.36% C, 8.76% H and 4.51% N. Infrared spectrum of neat oil shows stretch at ~3350 cm$^{-1}$, characteristic of lattice water (Nakamoto); 1600 cm$^{-1}$ region obscured by 4-(5-nonyl)pyridine stretches.

EXAMPLE 2

Determination of Solubility of $Cu(4-(5-nonyl)$ $pyridine)_2(HCOO)_2$ Complex in Supercritical Carbon Dioxide Solubility of the $Cu(4-(5-nonyl)pyridine)_2(HCOO)_2$ complex described in Example 1 was determined with an ISCO Model 3650 SCF Extractor. The complex (0.70 g) was thoroughly mixed with diatomaceous earth (0.70 g) in a Vacuum Atmospheres dry box under nitrogen to yield a royal blue solid mixture. This mixture was then loaded under nitrogen into a plastic sample container for the ISCO Model 3650 SCF Extractor. Supercritical carbon dioxide at 2500 psi and 40° C. was passed through the sample holder. A deep blue solution was recovered in methanol. The solubility was determined to be 4.3 wt % under these conditions. The instrument was programmed to heat the sample cell to 40° C. and pressurize it statically for 10 min, then flow liquid $CO_2$ feed through the sample vial at ~1 mL (liq)/min. The amount of the complex removed from the vial during the extraction was determined gravimetrically by weighing the chamber before and after the extraction. The amount of $CO_2$ delivered was taken from the ISCO syringe pump controller for the "dynamic" extraction and estimated by an assumed free volume in the chamber for the "static" extraction.

EXAMPLE 3

Copper Deposition from $Cu(4-(5-nonyl)pyridine)_2$ $(HCOO)_2$ Complex under 1000 psi Carbon Dioxide Deposition of copper from a solution of the of $Cu(4-(5-nonyl)pyridine)_2(HCOO)_2$ complex described in Example 1 was determined in the following manner. The complex (0.25 g) was dissolved in 10 mL hexane in a Vacuum Atmospheres dry box under nitrogen to yield a royal blue solution. This solution was placed in a tube and then heated to 120° C. under a final pressure of carbon dioxide of 1000 psi. This temperature and pressure were maintained for an hour. The tube was cooled to room temperature and vented. Copper metal was found deposited on the sides of the tube and copper powder was evident in the tube. Some of the copper was easily removed by wiping.

EXAMPLE 4

Solution Properties of Copper(II) Formate Complexes

This example is included to illustrate the determination of solution concentration by absorption spectroscopy. Some of the copper complexes used in this example are not examples of the invention.

The blue color of the copper(II) formate complexes permits determination of solution concentration by absorption spectroscopy through the use of Beer's law. Absorption spectra in the visible region were obtained with Hewlett Packard 8452A diode array spectrophotometer with HP ChemStation for UV-visible spectroscopy software. Compounds were prepared using the methods described in Examples 1–3. Solutions were prepared in a dry box with the protocols described in Example 1. 0.005–0.015 g of compound was dissolved in 5–15 mL of methanol. Spectra were recorded at 25° C. in quartz cuvette. Peak positions and molar absorptivity coefficients are shown in Table 2.

TABLE 2

Visible Absorption Data of Copper(II) Formate Complexes in Methanol

| Compound (solvent) | λ, nm | ε, M$^{-1}$cm$^{-1}$ |
|---|---|---|
| $Cu(4-(5-nonyl)pyridine)_2(HCOO)_2.H_2O$ | 696 | 54 |
| $Cu(2,6-lutidine)_2(HCOO)_2$ | 714 | 89 |
| $[Cu(1-methylimidazole)_2(HCOO)_2]_2$ | 654 | 49 |
| $Cu(1-butylimidazole)_2(HCOO)_2$ | 654 | 52 |
| $Cu((dibutylamino)propylamine)_2(HCOO)_2$ | 656 | 28 |

EXAMPLE 5

Synthesis of Copper (II) Complex of 1-octyl-2-ethyl-4-methylimidazole

The ligand, 1-octyl-2-ethyl-4-methylimidazole, was prepared in the following manner: 2-Ethyl-4-methylimidazole was dissolved in 10 ml anhydrous tetrahydrofuran (Aldrich 40,175-7, 99.9%, inhibitor-free). Sodium hydride (0.218 g) was added in portions as a solid; vigorous evolution of gas was evident with each addition. The resulting hazy, yellow solution was stirred overnight. 1-Bromooctane (1.568 mL) was added all at once. The mixture was refluxed for several hours. The mixture was filtered through diatomaceous earth. Solvent was removed under vacuum to produce yellow oil. Vacuum distillation of yellow oil produced clear, colorless oil. $^1$H NMR data (400 MHz, $CD_2Cl_2$); 6.55 (s, 1H); 3.75 (q, 2H); 2.65 (m, 2H); 2.2–2.15 (m, 3H); 1.3–1.8 (m, 15H); 0.9 (t, 3H).

Anhydrous copper formate was stirred in approximately 7 mL methanol. The imidazole derivative, 1-octyl-2-ethyl-4-methylimidazole, prepared as described above was dissolved in approximately 3 mL of methanol and then added all at once to the formate solution with vigorous stirring. A deep blue color developed immediately. The mixture was stirred for 0.5 hours and then filtered through diatomaceous earth. Removal of solvent yielded a blue oil, which is soluble in hexane as evidenced by the blue color of the hexane solution. Analysis was consistent with the formation of Cu(1-octyl-4-ethyl-2-methylimidazole)$_2$(HCOO)$_2$H$_2$O. Calculated: 58.46% C; 9.15% H and 9.09% N. Observed: 58.36% C, 9.12% H and 9.36% N. Infrared spectrum of neat oil shows stretch at 3333 cm$^{-1}$, characteristic of lattice water (Nakamoto).

EXAMPLE 6

Preparation of Cu(1-hexyl-2-ethyl-4-methylimidazole)$_2$(HCOO)$_2$.xH$_2$O.

1-Hexyl-2-ethyl-4-methylimidazole was prepared in the following manner. All manipulations were performed under a nitrogen atmosphere. 2-Ethyl-4-methylimidazole (1.0 g) was dissolved in 10 mL THF. Sodium hydride (0.218 g) was added as a solid. An additional 10 mL of solvent was used to wash the hydride into the flask. There was a vigorous evolution of hydrogen. Mixture was stirred at room temperature overnight. 1-Bromohexane (1.568 mL) was added all at once. Mixture was stirred over weekend at room temperature and then refluxed for several hours. Reaction mixture was cooled and then filtered through Celite 545. Solvent was stripped under vacuum to yield viscous, yellow oil. Proton NMR spectrum (E102868-78) is consistent with indicated formulation and starting 1-bromohexane. This mixture was used without purification.

The copper complex was prepared in the following manner. Anhydrous copper formate (0.079 g) was mixed in about 7 mL methanol. The yellow oil from the above preparation was dissolved in about 3 mL methanol and then added all at once to the stirred formate solution to yield a deep blue solution. The resulting mixture was stirred for five minutes and then filtered through Celite 545. The solvent was stripped to yield blue oil.

EXAMPLE 7

Preparation of Cu(1-octyl-2,5-dimethylpyrazole)$_2$ (HCOO)$_2$.

1-Octyl-3,5-dimethylpyrazole was prepared in the following manner. All manipulations were performed under a nitrogen atmosphere. 3,5-Dimethylpyrazole (5 g) was placed in a 100-mL 3-neck round-bottom flask with a magnetic stir bar and dissolved in 50 mL tetrahydrofuran. A condenser and stoppers were added. Sodium metal (1.2 g) was added in pieces. Hydrogen evolution was evident. Mixture was stirred at room temperature overnight. 1-Bromooctane (9 mL) was then added all at once. The mixture was brought to a gentle reflux for seven hours and then stirred overnight at room temperature. The reaction mixture was filtered through a sintered-glass frit to remove a white precipitate. Solvent was removed under vacuum. Product was distilled under vacuum. The fractions distilling at 65–70° C. were collected and used in subsequent preparations.

The copper (II) formate complex was prepared in the following manner. Anhydrous copper formate (0.185 g) was stirred in 10 mL methanol in a 50-mL Erlenmeyer flask. 1-Octyl-3,5-dimethylpyrazole 0.50 g) was added all at once as a methanol solution (3 mL). An additional 20 mL methanol were added. Reaction mixture was filtered through Celite 545. The solvent was removed under vacuum to yield green oil with some particulate. The mixture was dissolved in hexane and filtered. Removal of solvent gave a green oil. The process yields the title complex with additional pyrazole from incomplete reaction with copper formate. This material is suitable for deposition of copper films.

What is claimed is:

1. A composition comprising copper, two formate ions coordinated to the copper, and two aromatic nitrogen heterocyclic ligands coordinated to copper through nitrogen, wherein the aromatic nitrogen heterocyclic ligands are selected from the group consisting of $C_{10}$–$C_{20}$ alkyl-substituted pyridines, $C_9$–$C_{20}$ alkyl-substituted pyrazoles, $C_9$–$C_{20}$ alkyl-substituted imidazoles and $C_9$–$C_{20}$ alkyl-substituted triazoles, in which the N1 position of the pyrazole, imidazole and triazole ligands are alkyl-substituted.

2. The composition of claim 1 wherein the ligand is selected from the group of pyridines of Formula I:

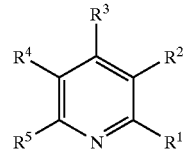

Formula I wherein $R^1$ and $R^5$ are selected from the group consisting of H and $C_1$–$C_4$ alkyl;

$R^2$ and $R^4$ are selected from the group consisting of H, $C_1$–$C_4$ straight-chain alkyl, and $C_6$–$C_{15}$ branched alkyl comprising at least one branch of at least four carbons; and $R^3$ is selected from the group consisting of H, $C_1$–$C_{15}$ straight chain alkyl and $C_6$–$C_{15}$ branched alkyl with at least one branch with at least four carbons in each branch with the proviso that at least one of $R^2$, $R^3$ and $R^4$ is $C_4$–$C_{15}$;

if $R^1$, $R^2$, $R^4$, and $R^5$ are each H, then $R^3$ is a $C_6$–$C_{15}$ straight chain alkyl or a nonyl branched alkyl, where at least one of the branches contains at least four carbons;

if either $R^1$ or $R^5$ is $C_4$ alkyl, then the other is H; and if $R^3$ is H or $C_1$, then at least one of $R^2$ and $R^4$ is $C_4$–$C_{15}$ straight chain alkyl or $C_6$–$C_{15}$ branched alkyl.

3. The composition of claim 1 wherein the ligand is selected from the group of pyrazoles of formula II:

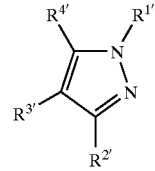

Formula II wherein, $R^{1'}$ is selected from the group consisting of Me and $C_6$–$C_{17}$ straight-chain alkyl and $C_6$–$C_{17}$ branched alkyl, with branches of at least four carbon atoms;

$R^{2'}$ and $R^{4'}$ are selected from the group consisting of H, $C_1$–$C_4$ straight-chain alkyl, and $C_3$–$C_4$ branched alkyl; and $R^{3'}$ is selected from the group consisting of H, $C_1$–$C_4$ straight-chain alkyl, $C_3$–$C_4$ branched alkyl, $C_6$–$C_{17}$ straight-chain alkyl and $C_6$–$C_{17}$ branched alkyl, with branches of at least four carbon atoms;

with the proviso that if $R^{2'}$, $R^{3'}$ and $R^{4'}$ are H, then $R^{1'}$ is $C_{10}$–$C_{17}$ straight chain alkyl or $C_6$–$C_{17}$ branched alkyl with branches of at least 4 carbon atoms.

4. The composition of claim 1 wherein the ligand is selected from the group of imidazoles of formula III:

Formula III

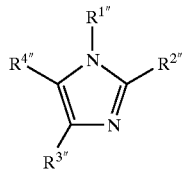

wherein,

R$^{1"}$ is selected from the group consisting of C$_1$–C$_8$ straight-chain alkyl and C$_6$–C$_8$ branched alkyl with at least one branch of at least four carbons;

R$^{4"}$ is selected from the group consisting of H, C$_1$–C$_8$ straight chain alkyl, and C$_6$–C$_8$ branched alkyl with at least one branch of four carbons; and R$^{2"}$ and R$^{3"}$ are selected from the group consisting of H, C$_1$–C$_4$ straight chain alkyl, and C$_3$–C$_4$ branched alkyl, with the provisos that at least one of R$^{1"}$ and R$^{4"}$ is C$_6$–C$_8$; and if R$^{2"}$, R$^{3"}$ and R$^{4"}$ are H, then R$^{1"}$ is C$_6$–C$_8$ branched alkyl with at least one branch of at least four carbons.

5. The composition of claim 1 wherein the ligand is selected from the group of triazoles of Formula IV:

Formula IV

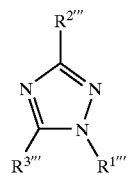

wherein,

R$^{1'''}$ is selected from the group of C$_8$–C$_{18}$ straight chain alkyl and C$_7$–C$_{18}$ branched alkyl with at least one branch of at least four carbons; and R$^{2'''}$ and R$^{3'''}$ are selected from the group consisting of H and C$_1$–C$_2$ alkyl.

6. The composition of claim 2, wherein the pyridine is selected from the group consisting of 4-(5-nonylpyridine) and 4-t-butylpyridine.

7. The composition of claim 3, wherein the pyrazole is selected from the group consisting of 1-octyl-3,5-dimethylpyrazole, 1-(2-ethylhexyl)pyrazole, 1-hexyl-3,5-dimethylpyrazole and 1-octylpyrazole.

8. The composition of claim 4 wherein the imidazole is selected from the group consisting of 1-octyl-2-ethyl-4-methylimidazole, 1-(2-ethylhexyl)-2-ethyl-4-methylimidazole, and 1-hexyl-2-ethyl-4-methylimidazole.

9. A process for deposition of metallic copper on a substrate or in or on a porous solid, comprising
  a. contacting the substrate or porous solid with a copper complex of claim 1 to form a copper complex-coated substrate; and
  b. heating the copper complex-coated substrate or porous solid to about 70° C. to about 200° C. to form a deposit of metallic copper on the substrate or porous solid.

10. The process of claim 9, further comprising a step of dissolving the copper complex in a non-polar solvent prior to contacting the substrate or porous solid with the copper complex.

11. The process of claim 10, wherein the non-polar solvent comprises supercritical carbon dioxide.

12. The process of claim 11, wherein the non-polar solvent further comprises a co-solvent selected from the group consisting of methanol, ethanol, propanol and butanol.

* * * * *